United States Patent [19]

Hrib et al.

[11] Patent Number: 4,780,466
[45] Date of Patent: Oct. 25, 1988

[54] ARYLPIPERAZINYLALKOXY DERIVATIVES OF CYCLIC IMIDES

[75] Inventors: Nicholas J. Hrib, Somerville; John G. Jurcak, Somerset, both of N.J.

[73] Assignee: Hoechst-Roussel Pharmaceuticals, Inc., Somerville, N.J.

[21] Appl. No.: 169,550

[22] Filed: Mar. 17, 1988

[51] Int. Cl.[4] ................ A61K 31/495; C07D 401/14; C07D 403/14; C07D 405/14
[52] U.S. Cl. .................... 514/254; 514/253; 544/230; 544/284; 544/295; 544/363; 544/364; 544/368; 544/376; 544/394
[58] Field of Search ............ 544/230, 295, 284, 363, 544/364, 368, 376, 394; 514/253, 254

[56] References Cited

U.S. PATENT DOCUMENTS

| | | | |
|---|---|---|---|
| 3,444,185 | 5/1969 | Nau et al. | 548/524 |
| 4,358,450 | 11/1982 | Gebert et al. | 544/376 |
| 4,367,335 | 1/1983 | Temple et al. | 544/295 |
| 4,423,049 | 12/1983 | Temple | 544/230 |
| 4,620,006 | 10/1986 | Sandefur et al. | 544/230 |
| 4,656,173 | 4/1987 | Yevich et al. | 544/230 |

FOREIGN PATENT DOCUMENTS 3615180 6/1986 Fed. Rep. of Germany .
51-125389 11/1986 Japan .

OTHER PUBLICATIONS

Yevich et al., "J. Med. Chem.", 1968, vol. 29, pp. 359–369.
Diehl et al., "J. Med. Chem.", vol. 8, 1965, pp. 274–275.

Primary Examiner—Glennon H. Hollrah
Assistant Examiner—James H. Turnipseed
Attorney, Agent, or Firm—Tatsuya Ikeda

[57] ABSTRACT

There are disclosed compounds of the formula $$\begin{array}{c} O \\ \parallel \\ C \\ A \diagdown \diagup \\ N-O-(CH_2)_n-N \diagdown N-R_3 \\ \diagup \diagdown \\ C \\ \parallel \\ W \end{array} \quad (I)$$

wherein the group A is $$R_1 \diagdown CH_2- \\ X \\ R_2 \diagup CH_2- \quad \text{or } (X)_p\text{-[phenyl]}$$

where $R_1$ and $R_2$ are each independently hydrogen or loweralkyl, or $R_1+R_2=(CH_2)_m$, m being 2 to 6, p is 1 or 2, and each X is independently hydrogen, loweralkyl, loweralkoxy, halogen, hydroxy, nitro, amino, loweralkylamino, diloweralkylamino, trifluoromethyl or loweralkylthio; W is O, $H_2$ or [H, OH]; n is 2, 3 or 4; and $R_3$ is

[phenyl-$(Y)_q$], [pyridyl-$(Y)_q$], [pyrimidinyl-$(Y)_q$], [benzofuran-$(Y)_q$], [benzothiophene-$(Y)_q$], [benzisoxazole-$(Y)_q$], [benzisothiazole-$(Y)_q$], [benzothiazole-$(Y)_q$], [naphthyl-$(Y)_q$], [quinolinyl-$(Y)_q$], [isoquinolinyl-$(Y)_q$] or [quinazolinyl-$(Y)_q$]

where q is 1 or 2 and each Y is independently hydrogen, loweralkyl, loweralkoxy, halogen, hydroxy, nitro, amino, loweralkylamino, diloweralkylamino, trifluoromethyl or loweralkylthio, which are useful as antipsychotic, anxiolytic and analgesic agents.

48 Claims, No Drawings

ARYLPIPERAZINYLALKOXY DERIVATIVES OF CYCLIC IMIDES

The present invention relates to compounds of formula I

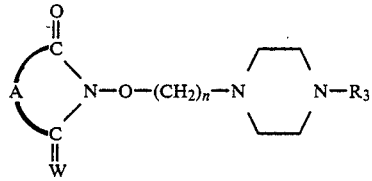

wherein the group A is

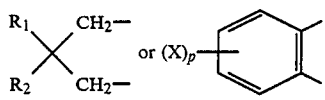

where $R_1$ and $R_2$ are each independently hydrogen or loweralkyl, or $R_1+R_2=(CH_2)_m$, m being 2 to 6, p is 1 or 2, and each X is independently hydrogen, loweralkyl, loweralkoxy, halogen, hydroxy, nitro, amino, loweralkylamino, diloweralkylamino, trifluoromethyl or loweralkylthio; W is O, $H_2$ or [H, OH]; n is 2, 3 or 4; and $R_3$ is

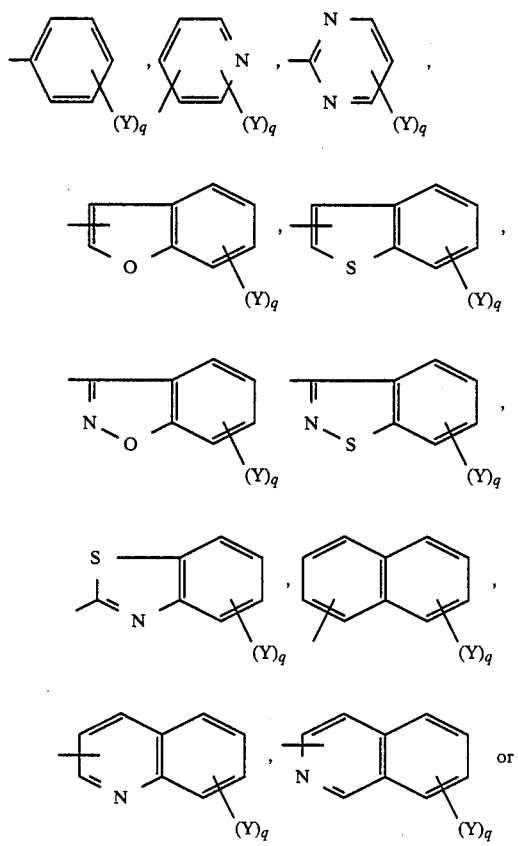

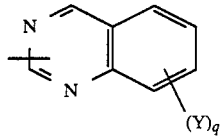

where q is 1 or 2 and each Y is independently hydrogen, loweralkyl, loweralkoxy, halogen, hydroxy, nitro, amino, loweralkylamino, diloweralkylamino, trifluoromethyl or loweralkylthio, which are useful as antipsychotic, anxiolytic and analgesic agents.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

The compounds of this invention having formula I are prepared by following one or more of the steps described below. Throughout the description of the synthetic steps, the definitions of A, $R_1$, $R_2$, m, p, X, W, n, $R_3$, q and Y are as given above unless otherwise stated or indicated.

STEP A

The compound of formula II is reacted with hydroxylamine hydrochloride to afford the compound of formula III.

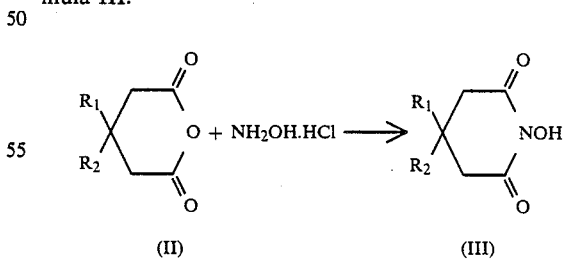

This reaction is typically conducted in a suitable medium such as anhydrous pyridine at a temperature of about 0° to 150° C., preferably under an inert gas atmosphere.

STEP B

Compound III is reacted with a dibromo compound of formula IV to afford a compound of formula V.

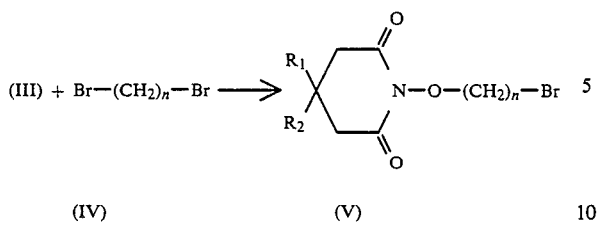

(IV)          (V)

This reaction is typically conducted in a suitable medium such as anhydrous acetonitrile and in the presence of an acid scavenger such as potassium or sodium carbonate or a tertiary amine and a catalyst such as sodium or potassium iodide and by stirring the reaction mixture at a temperature of about 25° to 80° C., preferably under an inert gas atmosphere.

STEP C

A compound of formula VI is reacted with compound IV in substantially the same manner as in STEP B above to afford a compound of formula VII.

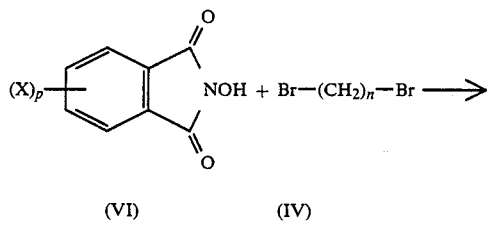

(VI)          (IV)

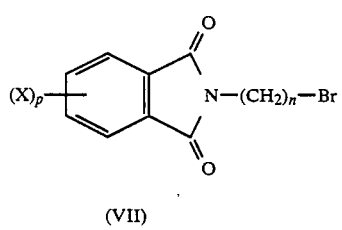

(VII)

STEP D

A compound of formula VIII obtained from STEP B or C above is reacted with a piperazine derivative of formula IX to afford a compound of formula Ia.

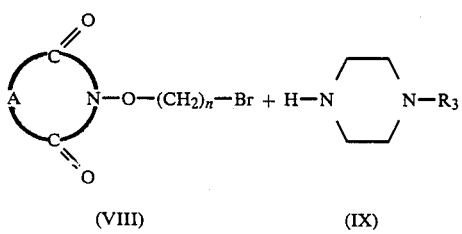

(VIII)          (IX)

This reaction is typically conducted in a suitable medium such as anhydrous acetonitrile and in the presence of an acid scavenger such as potassium or sodium carbonate and a catalyst such as sodium or potassium iodide and by stirring the reaction mixture at a temperature of 25° to 80° C., preferably under an inert gas atmosphere.

STEP E

Compound Ia is reacted with $NaBH_4$ to afford a compound of formula Ib.

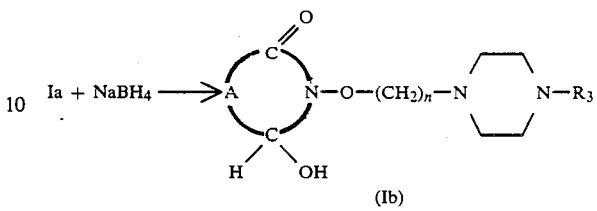

(Ib)

The above reaction is typically conducted in a suitable reaction medium including loweralkanols such as methanol, ethanol or isopropanol and mixtures of loweralkanols and other solvents such as dichloromethane or chloroform and at a temperature of 0° to 80° C.

STEP F

Compound Ib is reacted with a combination of a tri- or di-loweralkyl silane and an organic acid to afford a compound of formula Ic. The combination of triethylsilane and trifluoroacetic acid is most preferred.

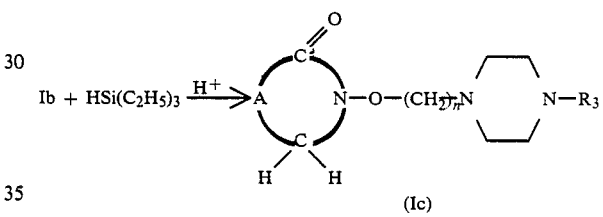

(Ic)

The above reaction is typically conducted in a suitable reaction system comprising, besides compound Ib, triethylsilane and trifluoroacetic acid, a solvent including chlorohydrocarbon such as dichloromethane and at a temperature of 0° to 25° C.

The compounds of the present invention having formula I are useful as antipsychotic agents.

Antipsychotic activity is determined in the climbing mice assay by methods similar to those described by P. Protais, et al., Psychopharmacol., 50, 1 (1976) and B. Costall, Eur. J. Pharmacol., 50, 39, (1978).

The subject CK-1 male mice (23-27 grams) are group-housed under standard laboratory conditions. The mice are individually placed in wire mesh stick cages (4'×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice With: | Score |
| --- | --- |
| 4 paws on bottom (no climbing) | 0 |
| 2 paws on the wall (rearing) | 1 |

| Climbing Behavior Mice With: | Score |
|---|---|
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By constrast, climbs due to mere motor stimulation usually last only a few seconds.

The climbing scores are individually totaled (maximum score: 6 per mouse over 3 readings) and the total score of the control group (vehicle intraperitoneally; apomorphine subcutaneously) is set to 100%. $ED_{50}$ values with 95% confidence limits, calculated by a linear regression analysis of some of the compounds of this invention are presented in Table 1.

TABLE 1

Antipsychotic Activity

| Compound | Climbing Mice Assay $ED_{50}$, mg/kg, ip |
|---|---|
| 8-[3-[4-(1,2-Benzisothiazol-3-yl)-1-piperazinyl]propyloxy]-8-azaspiro[4.5]-decan-7,9-dione hydrochloride hemihydrate | 5.7 |
| 8[3-[4-(3-Methoxyphenyl)-1-piperazinyl-propyloxy]-8-azaspiro[4.5]decan-7,9-dione hydrochloride hemihydrate (Reference compounds) | 10.9 |
| Clazapine | 8.1 |
| Sulpiride | 14.5 |

Antipsychotic response is achieved when the compounds of this invention are administered to a subject requiring such treatment as an effective oral, parenteral or intraveneous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not to any extent, limit the scope of practice of the invention Compounds I of the present invention are also useful as anxiolytic agents. The activity of the compounds is demonstrated in the Geller-conflict paradigm with rats. See Geller, Irving and Seifter, Psychopharmacologia Col. 1, 482–492 (1962). Male rats are used as test subjects. They are housed individually and food and water are available ad libitum until they are 300 to 400 grams prior to the start of training. Subsequently they are food deprived until their body weight is reduced to approximately 80% of original and it is maintained at this level by a restricted food diet.

The programming and test equipment consists of solid state devices, shockers and cages within sound-attentuated environmental enclosures. The data is recorded on both solid state print-out counters and cumulative recorders. The cages are equipped with a house-light, a single-lever, cue-lights, a liquid dipper, a speaker and a grid-floor connected to a shocker. Sweetened condensed milk delivered by the liquid-dipper serve as the positive reinforcement for all subjects.

The subjects are trained to lever-press for the milk reward in two distinct response-reward sections. In the anxiety or "conflict" segment, signaled by onset of both tone and cue-lights, a dipper of milk is delivered in response to each lever-press (CRF schedule of reinforcement). However lever presses during this period are also accompanied by a 40 m sec pulse of aversive footshock through the grid-floor. This creates a "conflict" between (1) easy access to milk reward and (2) the simultaneous presentation of a painful foot-shock. This "conflict" period is 3 minutes in duration.

During the other segment of this paradigm, the lever presses produces a dipper of milk only at variable intervals of time from 60 to 210 seconds with an average reward of once per 2 minutes (VI-2 in.). No shocks are ever administered during this VI phase of testing which is 15 minutes in duration.

The test procedure consists of four 15 minute (non-shock) VI segments where reinforcement was available on a limited basis. Each VI period is followed by a 3 minute "CRF"-conflict phase when reinforcement is constantly available but always accompanied by an aversive foot-shock. The shock-level is titrated for each subject to reduce the CRF responding to a total of less than 10 lever-presses during the entire test. The rats are tested four days a week. Drugs are administered on the third day and the performance is compared to the previous days control trials. The VI responses are used to evaluate any general debilitating drug effects, while the CRF responses are used to evaluate any "anti-anxiety" effects as indicated by increased responding during the "CRF-conflict" period.

All test compounds are administered by intraperitoneal injection in volumes of 10 cc/kg and the pretreat interval is usually one-half hour. Results of some of the compounds of this invention are presented in Table 2.

TABLE 2

Anxiolytic Activity

| Compound | Geller dose (mg/kg, i.p.)/ CRF ratio |
|---|---|
| 8-[3-[4-(3-Methylphenyl)-1-piperazinyl]propyloxy]-8-azaspiro[4.5]-decan-7,9-dione hydrochloride hemihydrate (Reference compound) | 10 mg/kg i.p./7.5 |
| Chlorodiazepoxide | 10 mg/kg i.p./3.6 |

Compounds of the present invention are also useful as analgesic agents due to their ability to alleviate pain in mammals. The activity of the compounds is demonstrated in the 2-phenyl-1,4-benzoquinone-induced writhing test in mice, a standard assay for analgesia, [Proc. Soc. Exptl. Biol. Med., 95,729 (1957)] Table 3 shows a result of the test of the analgesic activities of some of the compounds of this invention.

TABLE 3

Analgesic Activity

| Compound | (Phenylquinone Writhing) $ED_{50}$ mg/kg s.c. |
|---|---|
| 8-[3-[4-(1,2-Benzisothiazol-3-yl) -1-piperazinyl]propyloxy]-8-azaspiro | 0.9 |

TABLE 3-continued

Analgesic Activity

| | (Phenylquinone Writhing) ED$_{50}$ mg/kg s.c. |
|---|---|
| [4.5]decan,7,9-dione hydrochloride hemihydrate | |
| 8-[3-[4-(2-Methoxyphenyl)-1-piperazinyl-propyloxy]-8-azaspiro[4.5]decan-7,9-dione hydrochloride hemihydrate | 1.1 |
| (Reference compounds) | |
| Pentazocine | 1.3 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparatins should contain at least 0.5% of active compounds, but may be varied depending upon the particular form and may conveniently be between 4% to about 70% of the weight of the unit. The amount of active compound in such compositions in such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharamaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates an agents for the adjustment of tonicity such as sodium chloride or dextrose. The parenteral preparations can be enclosed indisposable syringes or multiple dose vials made of glass or plastic.

Examples of the compounds of this invention include:
8-[3-[4-(3-chlorophenyl)-1-piperazinyl]propyloxy]-8-azaspiro[4.5]decan-7,9-dione;
8-[3-[4-(3-methylphenyl)-1-piperazinyl]propyloxy]-8-azaspiro[4.5]decan-7,9-dione;
8-[3-[4-(2,3-dimethylphenyl)-1-piperazinyl]propyloxy]-8-azaspiro[4.5]decan-7,9-dione;
8-[3-[4-(3-trifluoromethylphenyl)-1-piperazinyl]propyloxy]-8-azaspiro[4.5]decan-7,9-dione;
8-[3-[4-(3-methoxyphenyl)-1-piperazinyl]propyloxy]-8-azaspiro[4.5]decan-7,9-dione;
8-[2-[4-(2-methoxyphenyl)-1-piperazinyl]ethoxy]-8-azaspiro[4.5]decan-7,9-dione;
8-[3-[4-(2-methoxyphenyl)-1-piperazinyl]propyloxy]-8-azaspiro[4.5]decan-7,9-dione;
8-[3-[4-(3-methylthiophenyl)-1-piperazinyl]propyloxy]-8-azaspiro[4.5]decan-7,9-dione;
8-[3-[4-(2-pyrimidinyl)-1-piperazinyl]propyloxy]-8-azaspiro[4.5]decan-7,9-dione;
8-[3-[4-(1,2-benzisothiazol-3-yl)-1-piperazinyl]propyloxy]-8-azaspiro[4.5]decan-7,9-dione;
8-[2-[4-(1,2-benzisothiazol-3-yl)-1-piperazinyl]ethoxy]-8-azaspiro[4.5]decan-7,9-dione;
8-[3-[4-(2-bensothiazolyl)-1-piperazinyl]propyloxy]-8-azaspiro[4.5]decan-7,9-dione;
N-[3-[4-(3-chlorophenyl)-1-piperazinyl]propyloxy]phthalimide;
N-[3-[4-(2-methylphenyl)-1-piperazinyl]propyloxy]phthalimide;
N-[3-[4-(3-methylphenyl)-1-piperazinyl]propyloxy]phthalimide;
N-[3-[4-(3-trifluoromethylphenyl)-1-piperazinyl]propyloxy]phthalimide;
N-[3-[4-(2-methoxyphenyl)-1-piperazinyl]propyloxy]phthalimide;
N-[3-[4-(3-methylthiophenyl)-1-piperazinyl]propyloxy]phthalimide;
N-[3-[4-(1,2-benzisothiazol-3-yl)-1-piperazinyl]propyloxy]phthalimide;
N-[3-[4-(2-quinolinyl)-1-piperazinyl]propyloxy]phthalimide;
8-[3-[4-(1,2-benzisothiazol-3-yl)-1-piperazinyl]propyloxy]-8-azaspiro[4.5]decan-7-one; and
8-[3-[4-(1-(2-methoxyphenyl)piperazinyl)propyloxy]]-8-azaspiro[4.5]decan-7-one.

The following examples are presented in order to illustrate this invention.

EXAMPLE 1

8-Hydroxy-8-azaspiro[4.5]decan-7,9-dione

A solution of 8-oxaspiro[4.5]decan-7,9-dione (5.0 g) and hydroxylamine hydrochloride (2.1 g) in 75 ml of anhydrous pyridine was heated to 80° C. with stirring under $N_2$.

After 18 hours the mixture was cooled to room temperature. The solids were filtered off and the filtrate was concentrated in vacuo. The residue was triturated exhaustively with $Et_2O$. The $Et_2O$ was concentrated in vacuo to provide 3.2 g of product as a white solid, homogeneous by TLC (thin layer chromatography), mp 69°–71°.

EXAMPLE 2

N-(3-Bromopropyloxy)phthalimide

To a solution of N-hydroxyphthalimide (2.0 g) and 1,3-dibromopropane (2.49 ml) in 50 ml of dry $CH_3CN$ was added diisopropylethylamine (4.27 ml). The mixture was stirred at room temperature. After 4 hours the volatiles were removed in vacuo. The residue was triturated with $Et_2O$ to provide 2.53 g of while solid, homogeneous by TLC.

ANALYSIS: Calculated for $C_{11}H_{10}BrNO_3$: 46.50%C, 3.54%H, 4.93%N. Found: 46.87%C, 3.50%H, 4.93%N.

EXAMPLE 3

8-(3-Bromopropyloxy)-8-azaspiro[4.5]decan-7,9-dione

A mixture of 8-hydroxy-8-azaspiro[4.5]decan-7,9-dione (5.22 g), 1,3-dibromopropane (5.8 ml), $K_2CO_3$ (3.9 g) and NaI (200 mg) in 100 ml of anhydrous $CH_3CN$ was heated with stirring at 80° under $N_2$.

After 6 hr no starting material remained as visualized by TLC (silica, ethyl acetate eluent). The mixture was cooled to room temperature, filtered and concentrated. The residue was chromatographed on silica using $CH_2Cl_2$ eluent to provide 3.7 g of product, homogeneous by TLC.

ANALYSIS: Calculated for $C_{12}H_{18}BrNO_3$: 47.38%C, 5.96%H, 4.60%N. Found: 47.42%C, 6.19%H, 4.46%N.

EXAMPLE 4

8-[3-[4-(3-Chlorophenyl)-1-piperazinyl]propyloxy]-8-azaspiro[4.5]decan-7,9-dione hydrochloride hemihydrate A solution of 8-(3-bromopropyloxy)-8-azaspiro[4.5]decan-7,9-dione (4.0 g) and 1-(3-chlorophenyl)piperazine hydrochloride (3.06 g) in 50 ml of $Et_3N$ was heated to reflux with stirring under $N_2$. After 1 hour TLC (thin layer chromatography) showed the absence of starting material. The excess $Et_3N$ was removed in vacuo and the residue chromatographed on silica using ethyl acetate as the eluent. Fractions containing the desired product were combined and concentrated in vacuo.

The HCl salt of the free amine was precipitated from $Et_2O$, collected and dried at 110° C. and 0.1 mm Hg pressure to provide a tan solid, mp 165°–168°.

ANALYSIS: Calculated for $C_{22}H_{30}ClN_3O_3.HCl.0.5-H_2O$: 56.77%C, 6.93%H, 9.03%N. Found: 56.55%C, 6.70%H, 8.81%N.

EXAMPLE 5

8-[3-[4-(3-Methylphenyl)-1-piperazinyl]propyloxy]-8-azaspiro[4.5]decan-7,9-dione hydrochloride hemihydrate A mixture of 8-(3-bromopropyloxy)-8-azaspiro[4.5]decan-7,9-dione (5.0 g), 1-(3-methylphenyl)piperazine dehydrochloride (4.11 g), $K_2CO_3$ (9.1 g), NaI (100 mg) and n-$Bu_4NBr$ (100 mg) in 100 ml of dry tolune was heated at 80° with stirring under $N_2$. After 4 hours, 50 ml of $CH_3CN$ was added. Heating was continued for 18 hr. and 5 ml of $Et_3N$ was added. Heating was continued for an additional 6 hr and at which time no starting material remained by TLC. The mixture was cooled to room temperature and filtered. The solvents were removed in vacuo and the residue was chromatographed on silica using ethyl acetate as the eluent. The fractions containing the desired product were combined and concentrated in vacuo.

The HCl salt of the free amine was precipitated from $Et_2O$, collected and dried at 110° and 0.1 mm Hg pressure to provide a white solid, mp 173°–175° (changes form at 113°–114°). Elemental analysis and NMR spectra indicated the hemihydrate structure.

ANALYSIS: Calculated for $C_{23}H_{33}N_3O_3.HCl.0.5-H_2O$: 62.07%C, 7.93%H, 9.44%N. Found: 61.85%C, 8.10%H, 9.29%N.

EXAMPLE 6

8-[3-[4-(2,3-Dimethylphenyl)-1-piperazinyl]propyloxy]-8-[4.5]decan-7,9-dione hydrochloride hemihydrate A mixture of 8-(3-bromopropyloxy)-8-azaspiro[4.5]decan-7,9-dione (4.0 g), 1-(2,3-dimethylphenyl)piperazine hydrochloride (1.71 g) and diisopropylethylamine (6.9 ml) in 100 ml of sieve-dried $CH_2Cl_2$ was heated to relux with stirring under $N_2$. After 6 hours, no starting material remained as judged by TLC. The mixture was cooled to room temperature and concentrated in vacuo.

The residue was chromatographed on silica using ethyl acetate as the eluent. The fractions containing the desired product were combined and concentrated in vacuo. The HCl salt of the free amine was precipitated from $Et_2O$, collected and dried at 110° and 0.1 mm Hg pressure. This provided a white powder, mp 188°–191° C. (darkened at 179° C.), homogeneous by TLC, which by elemental analysis and NMR was found to be a hemihydrate. The yield was 2.28 g.

ANALYSIS: Calculated for $C_{24}H_{35}N_3O_3.HCl.0.5-H_2O$: 62.79%C, 8.12%H, 9.15%N. Found: 62.32%C, 8.09%H, 9.09%N.

EXAMPLE 7

8-[3-[4-(3-Trifluoromethylphenyl)-1-piperazinyl]propyloxy]-8-azaspiro[4.5]decan-7,9-dione hydrochloride To a mixture of 8-(3-bromopropyloxy)-8-azaspiro[4.5]decan-7,9-dione (3.7 g) and 1-(3-trifluoromethylphenyl)piperazine in 100 ml of dry $CH_3CN$ were added $K_2CO_3$ (3.4g) and NaI (200 mg). The mixture was heated to 80° with stirring under $N_2$.

After 18 hours, the mixture was cooled to room temperature and filtered. The filtrate was concentrated in vacuo and the residue was chromatographed on silica using EtOAc as the eluent. The fractions containing the desired product were combined and concentrated in vacuo.

The HCl salt of the free amine was precipitated from Et$_2$O, collected and dried to give 3.95 g of product as a white solid. (Drying was conducted at 100°/0.1 mm Hg to remove one molecule of surface water.) The product was homogeneous by TLC and had a melting point of 200°–203°.

ANALYSIS: Calculated for C$_{23}$H$_{30}$F$_3$N$_3$O$_3$.HCl: 56.38%C, 6.38%H, 8.57%N. Found: 56.72%C, 6.35%H, 8.70%N.

EXAMPLE 8

8-[3-[4-(3-Methoxyphenyl)-1-piperazinyl]propyloxy]-8-azaspiro-[4.5]decan-7,9-dione hydrochloride hemihydrate A mixture of 8-(3-bromopropyloxy)-8-azaspiro[4.5]decan-7,9-dione (3.6 g), 1-(3-methoxyphenyl)-piperazine (2.28 g), K$_2$CO$_3$ (4.9 g) and NaI (200 mg) in 100 ml of anhydrous CH$_3$CN was heated to 80° with stirring under N$_2$ for 18 hr. The mixture was cooled to room temperature and filtered, the filtrate was concentrated in vacuo, taken up in Et$_2$O and filtered again, and the filtrate was concentrated in vacuo. The residue was chromatographed on silica. The fractions containing the desired product were combined and concentrated. The HCl salt of the free amine was precipitated from Et$_2$O, collected and dried. Recrystallization from CH$_2$Cl$_2$/Et$_2$O gave 0.83 g of product.

Further recrystallization from CH$_2$Cl$_2$/Et$_2$O provided a white solid, mp 192°–194° C. (dec), homogeneous by TLC which was shown by elemental analysis and NMR to process a hemihydrate structure.

ANALYSIS: Calculated for C$_{23}$H$_{33}$N$_3$O$_4$.HCl.0.5-H$_2$O: 59.92%C, 7.65%H, 9.11%N. Found: 60.07%C, 7.47%H, 8.78%N.

EXAMPLE 9

8-[3-[4-(3-Methylthiophenyl)-1-piperazinyl]propyloxy]-8-azaspiro[4.5]-decan-7,9-dione A mixture of 8-(3-bromopropyloxy)-8-azaspiro[4.5]decan-7,9-dione (4.0 g), 1-(3-methylthiophenyl)piperazine (2.75 g) and diisopropylethylamine (4.6 ml) was stirred in 100 ml of dry CH$_3$CN at room temperature under N$_2$.

After 18 hours no starting material remained as judged by TLC. The volatiles were removed in vacuo and the residue chromatographed on silica using EtOAc as the eluent. The fractions containing the desired product were combined and concentrated.

The HCl salt of the free amine was precipitated from Et$_2$O, but proved to be hygroscopic. The free base was extracted from saturated aqueous Na$_2$CO$_3$ with EtOAc and the extract was dried and concentrated.

After removal of the residual solvent at 0.1 mm Hg the free base solidified. Recrystallization from Et$_2$O provided 1.47 g of product, homogeneous by TLC, mp 86°–88°.

ANALYSIS: Calculated for C$_{22}$H$_{33}$N$_3$O$_3$S: 64.00%C, 7.71%H, 9.74%N. Found: 63.79%C, 7.72%H, 9.60%N.

EXAMPLE 10

8-[3-[4-(2-Pyrimidinyl)-1-piperazinyl]propyloxy]-8-azaspiro-[4.5]decan-7,9-dione hydrochloride hemihydrate To a mixture of 8-(3-bromopropyloxy)-8-azaspiro[4.5]decan-7,9-dione (4.0 g) and 1-(2-pyrimidinyl)-piperazine dihydrochloride (3.13 g) in 100 ml of dry CH$_3$CN were added K$_2$CO$_3$ (52.9 mmol) and NaI (200 mg). The mixture was heated to 80° with stirring under N$_2$.

After 18 hours the mixture was cooled to room temperature and filtered. The filtrate was concentrated in vacuo and the residue was chromatographed on silica using EtOAc as the eluent. The fractions containing the desired product were combined and concentrated.

The HCl salt of the free amine was precipitated from Et$_2$O, collected and dried to give 3.20 g of product as a white solid, mp 204°–206°, homogeneous by TLC.

ANALYSIS: Calculated for C$_{20}$H$_{29}$N$_5$O$_3$.HCl.0.5-H$_2$O: 55.48%C, 7.22%H, 16.17%N. Found: 55.84%C, 7.55%H, 16.13%N.

EXAMPLE 11

8-[3-[4-(1,2-Benzisothiazol-3-yl)-1-piperazinyl]-propyloxy]-8-azaspiro[4.5]decan-7,9-dione hydrochloride hemihydrate To a mixture of 8-(3-bromopropyloxy)-8-azaspiro[4.5]decan-7,9-dione (5.26 g) and 1-(1,2-benzisothiazol-3-yl)piperazine (3.8 g) in 100 ml of dry CH$_3$CN were added K$_2$CO$_3$ (4.8 g) and NaI (200 mg). The mixture was heated to 80° with stirring under N$_2$.

After 18 hours, the mixture was cooled to room temperature and filtered. The filtrate was concentrated in vacuo and the residue was chromatographed on silica using EtOAc as the eluent. The fractions containing desired product were combined and concentrated in vacuo.

The HCl salt of the free amine was precipitated from Et$_2$O, collected and dried to provide 3.42 g of product as a white solid, mp 207°–210° C., homogeneous by TLC. Elemental analysis and NMR spectra confirmed the structure as a hemihydrate.

ANALYSIS: Calculated for C$_{23}$H$_{30}$N$_4$O$_3$S.HCl.0.5-H$_2$O: 56.60%C, 6.61%H, 11.47%N, 7.25%Cl. Found: 56.28%C, 6.46%H, 11.42%N, 7.43%Cl.

EXAMPLE 12

8-[3-[4-(2-Benzothiazolyl)-1-piperazinyl]propyloxy]-8-azaspiro[4.5]decan-7,9-dione To a solution of 8-(3-bromopropyloxy)-8-azaspiro[4.5]decan-7,9-dione (5.0 g) and 1-(2-benzothiazolyl)piperazine (3.6 g) in 100 ml of anhydrous CH$_3$CN was added diisopropylethylamine (5.7 ml). The mixture was stirred at room temperature for 18 hours.

The mixture was then filtered and the filtrate was concentrated in vacuo. The residue was chromatographed on silica using EtOAc as the eluent. The fractions containing the desired product were combined and concentrated in vacuo, and the residual white solid was recrystallized from Et$_2$O to provide 1.5 g of product, mp 120°–123° C., homgeneous by TLC.

ANALYSIS: Calculated for C$_{23}$H$_{30}$N$_4$O$_3$S: 62.41%C, 6.83%H, 12.66%N. Found: 62.63%C, 6.82%H, 12.63%N.

EXAMPLE 13

N-[3-[4-(3-Chlorophenyl)-1-piperazinyl]propyloxy]phthalimide

To a solution of N-(3-bromopropyloxy)phthalimide (5.86 g) and 1-(3-chlorophenyl)piperazine dihydrochloride (5.6g) in 100 ml of anhydrous CH$_3$CN was added diisopropylethylamine (18.0 ml). The mixture was stirred at room temperature under N$_2$.

After 18 hours no starting bromide remained as judged by TLC. The volatiles were removed in vacuo and the residue was chromatographed on silica using EtOAc as the eluent. The fractions containing the desired product were combined and concentrated in vacuo. The residual solid was recrystallized from $CH_2Cl_2/Et_2O$ to provide 4.01 g of product as white needles, homogeneous by TLC, mp 140°–142° C.

ANALYSIS: Calculated for $C_{21}H_{22}ClN_3O_3$: 63.07%C, 5.55%H, 10.51%N. Found: 63.06%C, 5.63%H, 10.78%N.

EXAMPLE 14

N-[3-[4-(2-Methylphenyl)-1-piperazinyl]propyloxy]phthalimide

A mixture of 1-(3-bromopropyloxy)phthalimide (4.75 g), 1-(2-methylphenyl)piperazine dihydrochloride (4.18 g) and diisopropylethylamine (11.7 ml) in 100 ml of dry $CH_3CN$ was stirred at room temperature under $N_2$.

After 18 hours no starting material remained as judged by TLC. The volatiles were removed in vacuo and the residue was chromatographed on silica using EtOAc as the eluent. The fractions containing the desired product were combined and concentrated, and the residual solid was recrystallized from $CH_2Cl_2/Et_2O$ to provide 2.48 g of product, homogeneous by TLC, mp 174°–176° C.

ANALYSIS: Calculated for $C_{22}H_{25}N_3O_3$: 69.63%C, 6.64%H, 11.10%N. Found: 69.44%C, 6.76%H, 11.03%N.

EXAMPLE 15

N-[3-[4-(3-Methylphenyl)-1-piperazinyl]propyloxy]phthalimide

To a suspension of N-(3-bromopropyloxy)phthalimide (5.0 g) and 1-(3-methylphenyl)piperazine dihydrochloride (4.38 g) in 100 ml of dry $CH_3CN$ was added diisopropylethylamine (12.3 ml). The mixture was stirred at room temperature under $N_2$.

After 18 hours no starting bromide remained as judged by TLC. The volatiles were removed in vacuo and the residue was chromatographed on silica using EtOAc as the eluent. The fractions containing the desired product were combined and concentrated in vacuo. This provided a white solid which was recrystallized from $CH_2Cl_2/Et_2O$ to provide 3.02 g of product, mp 127°–128° C., homogeneous by TLC.

ANALYSIS: Calculated for $C_{22}H_{25}N_3O_3$: 69.63%C, 6.64%H , 11.07%N. Found: 69.53%C, 6.74%H, 10.96%N.

EXAMPLE 16

N-[3-[4-(3-Trifluoromethylphenyl)-1-piperazinyl]propyloxy]phthalimide hydrochloride To a solution of N-(3-bromopropyloxy)phthalimide (3.0 g) and 1-(3-trifluoromethylphenyl)piperazine (2.4 g) in 100 ml of anhydrous $CH_3CN$ was added diisopropyl ethylamine (3.7 ml). The solution was stirred at room temperature under $N_2$.

After 18 hours no starting bromide remained as judged by TLC. The volatiles were removed in vacuo and the residue was chromatographed on silica using EtOAc as the eluent. The fractions containing the desired product were combined and concentrated. The HCl salt of the free amine was precipitated from $Et_2O$ to provide 2.6 g of white powder. This was recrystallized from $CH_2Cl_2/Et_2O$ to provide 1.92 g of product, mp 161°–164° C., homogeneous by TLC.

ANALYSIS: Calculated for $C_{22}H_{22}F_3N_3O_3 \cdot HCl$: 56.23%C, 4.93%H, 8.94%N, 7.54%Cl. Found: 56.16%C, 5.22%H, 8.82%N, 7.32%Cl.

EXAMPLE 17

N-[3-[4-(2-Methoxyphenyl)-1-piperazinyl]propyloxy]phthalimide

To a suspension of N-(3-bromopropyloxy)phthalimide (4.0 g) and 1-(2-methoxyphenyl)piperazine hydrochloride (3.23 g) in 100 ml of dry $CH_3CN$ was added diisopropylethylamine (7.4 ml). The mixture was stirred at room temperature under $N_2$.

After 4 hours, no starting bromide remained as judged by TLC. The volatiles were removed in vacuo and the residue was triturated with EtOAc and filtered. The EtOAc was removed in vacuo to provide 6.7 g of crude product which was chromatographed on silca using EtOAc as the eluent. The fractions containing the desired product were combined and concentrated in vacuo. The residual solid was recrystallized from $EtOAc/Et_2O$ to provide 3.20 g of a white solid, mp 141°–143° C., homogeneous by TLC.

ANALYSIS Calculated for $C_{22}H_{25}N_3O_4$: 66.82%C, 6.37%H, 10.63%N. Found: 66.57%C, 6.35%H, 10.44%N.

EXAMPLE 18

N-[3-[4-(3-Methylthiophenyl)-1-piperazinyl]propyloxy]phthalimide

A solution prepared from N-(3-bromopropyloxy)phthalimide (5.00 g), 1-(3-methylthiophenyl)piperazine (3.85 g), diisopropylethylamine (4.55 g) and $CH_3CN$ (150 ml) was stirred at room temperature under $N_2$ for 84 hr. The solution was concentrated in vacuo and dried under vacuum yielding 10.5 g of a foam. TLC analysis showed one major product. The foam was extracted with EtOAc (250 ml) yielding after concentration 7.1 g of an oil. The oil was chromatographed (2 silica gel columns) to provide 4.00 g of an oil. The oil was triturated with $EtOAc/Et_2O$ to give a solid which was recrystallized from $EtOAc/Et_2O$ yielding 3.08 g of crystals, mp 103°–106° C.

ANALYSIS Calculated for $C_{22}H_{25}N_3O_3S$: 64.21%C, 6.12% H, 10.21%N. Found: 64.29%C, 6.10%H, 10.34%N.

EXAMPLE 19

N-[3-[4-(1,2-Benzisothiazol-3-yl)-1-piperazinyl]propyloxy]phthalimide

To a solution of N-(3-bromopropyloxy)phthalimide (4.0 g) and 1-(1,2-benzisothiazol-3-yl)piperazine (3.09 g) in 100 ml of dry $CH_3CN$ was added diisopropylethylamine (5.0 ml). The mixture was stirred at room temperature under $N_2$.

After 18 hours no starting bromide remained as judged by TLC. The volatiles were removed in vacuo and the residue was chromatographed on silica using 10:90 hexane/EtOAc as the eluent. The fractions containing the desired product were combined and concentrated in vacuo. The residual solid was recrystallized from $CH_2Cl_2Et_2O$ to provide 2.88 g of white fine crystals, homogeneous by TLC, mp 143°–144.5° C.

ANALYSIS: Calculated for $C_{22}H_{22}N_4O_3S$: 62.54%C, 5.25%H, 13.26%N. Found: 62.25%C, 5.30%H, 13.48%N.

EXAMPLE 20

N-[3-[4-(2-Quinolinyl)-1-piperazinyl]propyloxy]phthalimide

To a solution of N-(3-bromopropyloxy)phthalimide (5.41 g) and 1-(2-quinolinyl)piperazine (4.07 g) in 100 ml of anhydrous CH$_3$CN was added diisopropylethylamine (6.7 ml). The mixture was stirred at room temperature under N$_2$.

After 18 hours no starting bromide remained as judged by TLC. The volatiles were removed in vacuo and the residue was chromatographed on silica using EtOAc as the eluent. The fractions containing the desired product were combined and concentrated in vacuo. The residual solid was recrystallized from CH$_2$Cl$_2$/Et$_2$O to provide 3.79 g of product as a white solid, homogeneous by TLC, mp 158°–160° C.

ANALYSIS: Calculated for C$_{24}$H$_{24}$N$_4$O$_3$: 69.21%C, 5.81%H, 13.45%N. Found: 69.20%C, 5.79%H, 13.58%N.

EXAMPLE 21

8-[3-[4-(2-Quinolinyl)-1-piperazinyl]propyloxy]-8-azaspiro[4.5]decan-7,9-dione

A mixture of 8-(3-bromopropyloxy)-8-azaspiro[4.5]decan-7,9-dione (5.7 g), 1-(2-quinolinyl)piperazine (4.0 g) and diisopropylethylamine (6.6 ml) in 100 ml of dry CH$_3$CN was heated to 80° with stirring under N$_2$.

After 18 hours, the mixture was cooled to room temperature, filtered and concentrated in vacuo. The residue was chromatographed on silica using EtOAc as the eluent. The fractions containing the desired product were combined and concentrated. The residual solid was recrystallized from hexane/Et$_2$O to provide 2.17 g of product, mp 103°–106° C., homogeneous by TLC (silica).

ANALYSIS: Calculated for C$_{25}$H$_{32}$N$_4$O$_3$: 68.78%C, 7.39%H, 12.83%N. Found: 69.05%C, 7.60%H, 12.85%N.

EXAMPLE 22

8-[3-[4-(1,2-Benzisothiazol-3-yl)-1-piperazinyl]-propyloxy]-7-hydroxy-8-azaspiro [4.5]decan-9-one To a solution prepared from 8-[3-[4-(1,2-benzisothiazol-3-yl)-1-piperazinyl]propyloxy]-8-azaspiro[4.5]decan-7,9-dione (4.25 g), 80 ml of CH$_3$OH and 20 ml of CH$_2$Cl$_2$ was added with stirring NaBH$_4$ (1.52 g) in one portion. The mixture was stirred at room temperature for 1 hr and thereafter quenched with a solution prepared from 2 ml of 20% aqueous KOH and 50 ml of H$_2$O.

The organic phase was drawn off and the aqueous phase was extracted with CH$_2$Cl$_2$. The combined organic phases were dried over MgSO$_4$ and concentrated in vacuo to give 3.92 g of a yellow foam. This crude material was chromatographed on silica using CH$_3$OH/EtOAc (5:95) eluent to provide first 360 mg of unreacted starting material followed by the desired product. The product was crystallized from Et$_2$O and dried to provide 2.340 g of white solid, mp 135°–157°, homogeneous by TLC (silica).

ANALYSIS: Calculated for C$_{23}$H$_{32}$N$_4$OS: 62.13%C, 7.26%H, 12.60%N. Found: 62.10%C, 7.28%H, 12.49%N.

EXAMPLE 23

8-3-[4-(1,2-Benzisothiazol-3-yl)-1-piperazinyl]propyloxy]-8-azaspiro[4.5]decan-7-one hydrochloride To a solution prepared from 8-[3-[4-(1,2-benzisothiazol-3-yl)-1-piperazinyl]propyloxy]-7-hydroxy-8-azaspiro[4.5]decan-9-one (4.7 g), 80 ml of CH$_2$Cl$_2$ and 40 ml of trifluoroacetic acid was added triethylsilane (1.8 ml) dropwise. The mixture was stirred at room temperature. After 1.5 hours, no starting material remained as judged by TLC.

The volatiles were removed in vacuo. The residue was diluted with EtOAc, washed first with saturated aqueous Na$_2$CO$_3$, then with brine. The organic phase was dried over MgSO$_4$, filtered and concentrated.

The residue was chromatographed on silica with CH$_3$OH/EtOAc (5:95) used as the eluent. The fractions containing the desired product were combined and concentrated. Attempts to crystallize the free base failed. The HCl salt of the free base was precipitated from Et$_2$O and recrystallized from CH$_2$Cl$_2$/EtOAc/hexane to provide 1.360 g of product as needles, mp 194°–197°, homogeneous by TLC (silica).

ANALYSIS: Calculated for C$_{23}$H$_{32}$N$_4$O$_2$S.HCl: 59.39%C, 7.15%H, 12.05%N. Found: 58.93%C, 7.14%H, 11.74%N.

EXAMPLE 24

8-[3-[4-(2-Methoxyphenyl)-1-piperazinyl]propyloxy]-7-hydroxy-8-azaspiro[4.5]decan9-one To a solution prepared from 8-[3-[4-(3-methoxyphenyl)-1-piperazinyl]propyloxy]-8-azaspiro[4.5]decan-7,9-dione (5.0 g), 300 ml of CH$_3$OH and 100 CH$_2$Cl$_2$ was added NaBH$_4$ (1.8 g) with stirring. The mixture was stirred at room temperature.

After 18 hours, the mixture was quenched with a solution prepared from 2 ml of 20% aqueous KOH and 100 m of H$_2$O. The mixture was extracted with CH$_2$Cl$_2$, and the organic fractions were combined, dried over MgSO$_4$, filtered and concentrated in vacuo.

The residue was chromatographed on silica with CH$_3$OH/EtOAc (10:90) used as the eluent. Fractions containing the desired product were combined and concentrated in vacuo. This provided a viscous oil which was recrystallized from Et$_2$O/hexane to provide 1.949 g of white crystals, mp 107°–110°, homogeneous by TLC (silica).

ANALYSIS: Calculated for C$_{23}$H$_{35}$N$_3$O$_4$: 66.16%C, 8.45%H, 10.06%N. Found: 65.92%C, 8.38%H, 10.09%N.

EXAMPLE 25

8-[3-[4-(2-Methoxyphenyl)-1-piperazinyl]propyloxy]-8-azaspiro[4.5]decan-7-one hydrochloride sesquihydrate To a solution prepared from 8-[3-[4-(2-methoxyphenyl)1-piperazinyl]propyloxy]-7-hydroxy-8-azaspiro[4.5]decan-9-one, 60 ml of CH$_2$Cl$_2$ and 30 ml of trifluoroacetic acid was added triethylsilylane (1.26 ml) in one portion. The mixture was stirred at room temperature for 1.5 hours.

The solvents were then removed in vacuo. The residue was diluted with 100 ml of 5% aqueous KOH and extracted with EtOAc. The combined organic phases were washed successively with 10% aqueous KOH and brine, dried over MgSO$_4$ and concentrated. Removal of the solvent gave 3.09 g of crude material which was recrystallized from Et$_2$O. This material (2.2 g) proved to be the trifluroacetate salt. The base was freed by partitioning between EtOAc/saturated aqueous Na$_2$CO$_3$. The organic phase was dried (MgSO$_4$) and concentrated in vacuo. The HCl salt of the free base was precipitated from Et$_2$O/CH$_2$Cl$_2$ to provide 1.436 g of white crystals, mp 140°–142°. Elemental analysis and NMR indicated a 1.5 hydrate structure.

ANALYSIS: Calculated for C$_{23}$H$_{35}$N$_3$O$_3$.HCl.1.5-H$_2$O: 59.40%C, 8.45%H, 9.03%N, Found: 59.52%C, 8.26%H, 8.86%N.

EXAMPLE 26

8-(2-Bromoethyloxy)-8-azaspiro[4.5]decan-7,9-dione

To a solution of 8-hydroxy-8-azaspiro[4.5]decan-7,9-dione (30 g) in 600 ml of dry CH₃CN were added diisopropylethylamine (57 ml) and 1,2-dibromoethane (42.4 ml). The mixture was heated to 70° with stirring. After 7 hours, heating was discontinued and the mixture was stirred at room temperature for 48 hours.

The volatiles were removed in vacuo and the residue was taken up in ethyl acetate, filtered and concentrated in vacuo. The residue was chromatographed on silica using CH₂Cl₂ as the eluents and the elute was recrystallized from a small amount of diethyl ether to obtain 25.57 g of product as white crystals, mp 75°–77°.

ANALYSIS: Calculated for $C_{11}H_{16}BrNO_3$: %C, %H, %N. Found: %C, %H, %N.

EXAMPLE 27

8-[2-[4-(2-Methoxyphenyl)-1-piperazinyl]ethoxy]-8-azaspiro[4.5]decan-7,9-dione dihydrochloride A mixture of 8-(2-bromoethyloxy)-8-azaspiro[4.5]decan-7,9-dione (4.0 g), 1-(2-methoxyphenyl)piperazine hydrochloride (3.16 g), K₂CO₃ (5.7 g) and NaI (200 mg) was heated to 80° with stirring in 150 ml of anhydrous CH₃CN under N₂.

After 18 hours, no starting piperazine remained as judged by TLC. The mixture was cooled to room temperature and filtered. The filtrate was concentrated in vacuo, and the residue was taken up in ethyl acetate, washed with H₂O, dried, (MgSO₄), filtered and again concentrated in vacuo. This residue was chromatographed on silica using ethyl acetate as the eluent to provide the products as an oil which was taken up in diethyl either. The dihydrochloride salt of this product was precipitated from diethyl ether and recrystallized from EtOAc/CH₂Cl₂ to provide 3.98 g of product as white crystals, homogeneous by TLC, mp. 176°–179° C.

ANALYSIS: Calculated for $C_{22}H_{31}N_3O_4.2HCl$: 55.69%C, 7.01%H, 8.85%N. Found: 55.58%C, 7.16%H, 8.77%N.

EXAMPLE 28

8-[2-[4-(1,2-Benzisothiazol-3-yl)-1-piperazinyl]ethoxy]-8-azaspiro[4.5]decan-7,9-dione A mixture of 8-(2-bromoethyloxy)-8-azaspiro[4.5]decan-7,9-dione (3.7 g), 1-(1,2-benzisothiazol-3-yl)piperazine (2.2 g), K₂CO₃ (2.77 g) and NaI (200 mg) was heated with stirring in 125 mil of anhydrous CH₃CN under N₂.

After 18 hours, no starting material remained as judged by TLC. The mixture was cooled to room temperature and filtered. The filtrate was concentrated in vacuo, and the residue chromatographed on silica first with EtOAc and then with 1:99 CH₃OH/EtOAc used as eluents to provide the product, which solidified on removal of the solvent in vacuo.

The solid was recrystallized from Et₂O/CH₂Cl₂ to afford 2.33 g of white crystals, mp 150°–152° C.

ANALYSIS: Calculated for $C_{22}H_{28}N_4O_3S$: 61.65%C, 6.58%H, 13.07%N. Found: 61.45%C, 6.68%H, 12.98%N.

We claim:

1. A compound of the formula

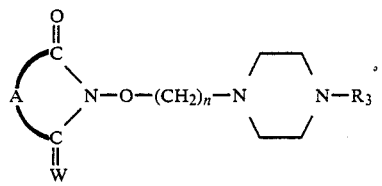

wherein the group A is

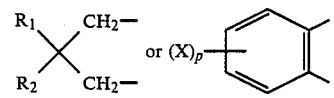

where $R_1$ and $R_2$ are each independently hydrogen or loweralkyl, or $R_1+R_2=(CH_2)_m$, m being 2 to 6; p is 1 or 2, and each X is independently hydrogen, loweralkyl, loweralkoxy, halogen, hydroxy, nitro, amino, loweralkylamino, diloweralkylamino, trifluoromethyl or loweralkylthio; W is O, H₂ or [H, OH]; n is 2, 3 or 4; and $R_3$ is

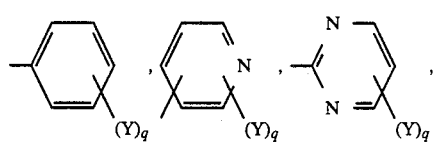

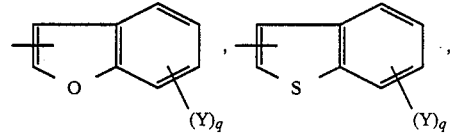

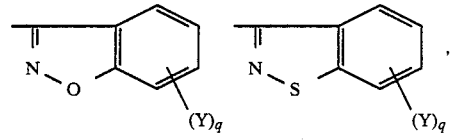

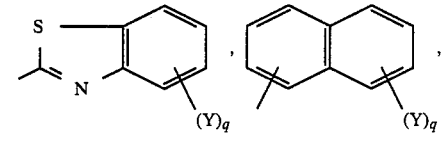

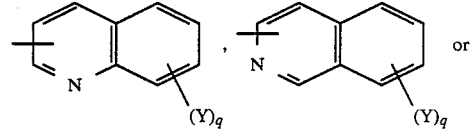

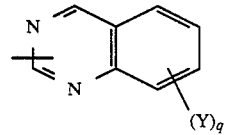

where q is 1 or 2 and each Y is independently hydrogen, loweralkyl, loweralkoxy, halogen, hydroxy, nitro, amino, loweralkylamino, diloweralkylamino, trifluoromethyl or loweralkylthio; or a pharmaceutically acceptable acid addition salt thereof.

2. The compound as defined in claim 1, where n is 3.
3. The compound as defined in claim 1, where n is 2.
4. The compound as defined in claim 2, where A is

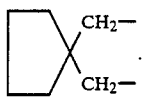

5. The compound as defined in claim 2, where A is

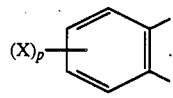

6. The compound as defined in claim 5, where X is hydrogen.
7. The compound as defined in claim 2, where W is O.
8. The compound as defined in claim 2, where W is H$_2$.
9. The compound as defined in claim 2, where W is [OH, H].
10. The compound as defined in claim 4, where W is O.
11. The compound as defined in claim 4, where W is H$_2$.
12. The compound as defined in claim 4, where W is [OH, H].
13. The compound as defined in claim 5, where W is O.
14. The compound as defined in claim 5 where W is H$_2$.
15. The compound as defined in claim 3, where A is

16. The compound as defined in claim 3, where W is O.
17. The compound as defined in claim 3, where A is

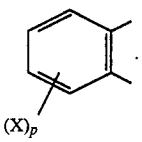

18. The compound as defined in claim 17, where X is hydrogen.
19. The compound as defined in claim 1, which is 8-[3-[4-(3-chlorophenyl)-1-piperazinyl]propyloxy]-8-azaspiro[4.5]decan-7,9-dione.
20. The compound as defined in claim 1, which is 8-[3-[4-(3-methylphenyl)-1-piperazinyl]propyloxy]-8-azaspiro[4.5]decan-7,9-dione.
21. The compound as defined in claim 1, which is 8-[3-[4-(2,3-dimethylphenyl)-1-piperazinyl]propyloxy]-8-azaspiro[4.5]decan-7,9-dione.
22. The compound as defined in claim 1, which is 8-[3-[4-(3-trifluoromethylphenyl)-1-piperazinyl]-propyloxy]-8-azaspiro[4.5]decan-7,9-dione.
23. The compound as defined in claim 1, which is 8-[3-[4-(3-methoxyphenyl)-1-piperazinyl]propyloxy]-8-azaspiro[4.5]-decan-7,9-dione.
24. The compound as defined in claim 1, which is 8-[3-[4-(3-methylthiophenyl)-1-piperazinyl]propyloxy]-8-azaspiro[4.5]decan-7,9-dione.
25. The compound as defined in claim 1, which is 8-[3-[4-(2-pyrimidinyl)-1-piperazinyl]propyloxy]-8-azaspiro[4.5]decan-7,9-dione.
26. The compound as defined in claim 1, which is 8-[3-[4-(1,2-benzisothiazol-3-yl)-1-piperazinyl]-propyloxy]-8-azaspiro[4.5]decan-7,9-dione.
27. The compound as defined in claim 1, which is 8-[3-[4-(2-benzothiazolyl)-1-piperazinyl]propyloxy]-8-azaspiro[4.5]decan-7,9-dione.
28. The compound as defined in claim 1, which is [3-[4-(2-methoxyphenyl)-1-piperazinyl]propyloxy]-8-azaspiro[4.5]decan-7,9-dione.
29. The compound as defined in claim 1, which is 8-[2-[4-(1,2-benzisothiazol-3-yl)-1-piperazinyl]ethoxy]-8-azaspiro[4.5]-7,9-dione.
30. The compound as defined in claim 1, which is 8-[2-[4-(2-methoxyphenyl)-1-piperazinyl]ethoxy]-8-azaspiro[4.5]decan-7,9-dione;
31. The compound as defined in claim 1, which is 8-[2-[4-(2-pyrimidinyl)-1-piperazinyl]ethoxy-8-azaspiro[4.5]decan-7,9-dione;
32. The compound as defined in claim 1, which is N-[3-[4-(3-chlorophenyl)-1-piperazinyl]propyloxy]phthalimide.
33. The compound as defined in claim 1, which is N-[3-[4-(2-methylphenyl)-1-piperazinyl]propyloxy]phthalimide.
34. The compound as defined in claim 1, which is N-[3-[4-(3-methylphenyl)-1-piperazinyl]propyloxy]phthalimide.
35. The compound as defined in claim 1, which is N-[3-[4-(3-trifluoromethylphenyl)-1-piperazinyl]-propyloxy]phthalimide.
36. The compound as defined in claim 1, which is N-[3-[4-(2-methoxyphenyl)-1-piperazinyl]propyloxy]phthalimide.
37. The compound as defined in claim 1, which is N-[3-[4-(3-methylthiophenyl)-1-piperazinyl]propyloxy]phthalimide.
38. The compound as defined in claim 1, which is N-[3-[4-(1,2-benzisothiazol-3-yl)-1-piperazinyl]-propyloxy]phthalimide.
39. The compound as defined in claim 1, which is N-[3-[4-(2-quinolinyl)-1-piperazinyl]propyloxy]phthalimide.
40. The compound as defined in claim 1, which is 8-[3-[4-(2-quinolinyl)-1-piperazinyl]propyloxy]-8-azaspiro[4.5]decan-7,9-dione.
41. The compound as defined in claim 1, which is 8-[3-[4-(1,2-benzisothiazol-3-yl)-1-piperazinyl]-propyloxy]-7-hydroxy-8-azaspiro[4.5]decan-9-one.
42. The compound as defined in claim 1, which is 8-[3-[4-(1,2-benzisothiazol-3-yl)-1-piperazinyl]-propyloxy]-8-azaspiro[4.5]decan-7-one.
43. The compound as defined in claim 1, which is 8-[3-[4-(2-methoxyphenyl)-1-piperazinyl]propyloxy]-7-hydroxy-8-azaspiro[4.5]decan-9-one.

44. The compound as defined in claim 1, which is 8-[3-[4-(2-methoxyphenyl)-1-piperazinyl]propyloxy]-8-azaspiro[4.5]decan-7-one.

45. An antipsychotic composition comprising an effective psychosis alleviating amount of a compound as defined in claim 1 and a suitable carrier therefor.

46. An anxiolytic composition comprising an effective anxiety alleviating amount of a compound as defined in claim 1 and a suitable carrier therefor.

47. An analgesic composition an effective pain alleviating amount of a compound as defined in claim 1 and a suitable carrier therefor.

48. A method of alleviating psychosis in a patient suffering from psychosis which comprises administering an effective psychosis alleviating amount of a compound as defined in claim 1.

* * * * *